United States Patent
Bae et al.

(10) Patent No.: US 7,371,781 B2
(45) Date of Patent: *May 13, 2008

(54) TUMOR ENVIRONMENT-INDUCED LIGAND-EXPRESSING NANOCARRIER SYSTEM

(75) Inventors: You Han Bae, Salt Lake City, UT (US); Kun Na, Salt Lake City, UT (US); Eun Seong Lee, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 75 days.

This patent is subject to a terminal disclaimer.

(21) Appl. No.: 10/948,078

(22) Filed: Sep. 22, 2004

(65) Prior Publication Data
US 2005/0118252 A1    Jun. 2, 2005

Related U.S. Application Data

(60) Provisional application No. 60/505,227, filed on Sep. 22, 2003.

(51) Int. Cl.
*A61K 47/00* (2006.01)
(52) U.S. Cl. .................... 514/772.1; 424/400; 514/772
(58) Field of Classification Search ...................... None
See application file for complete search history.

(56) References Cited

U.S. PATENT DOCUMENTS 5,543,158 A * 8/1996 Gref et al. ............... 424/501

OTHER PUBLICATIONS

Huh et al., Polymer 40 (1999) 6147-6155.*
Salem et al, Advanced Materials 15 (2003) 210-213.*
Gref et al., Biomaterials 23 (2003) 4529-4537.*
Eun Seong Lee et al., Polymeric micelle for tumor pH and folate-mediated targeting, Journal of Controlled Release, 2003, pp. 103-113, vol. 91.
Eun Seong Lee et al., Poly(L-histidine)-PEG block copolymer micelles and pH-induced destabilization, Journal of Controlled Release, 2003, pp. 363-374, vol. 90.
Kun Na et al., Self-Assembled Hydrogel Nanoparticles Responsive to Tumor Extra Cellular pH from Pullulan Derivative/Sulfonamide Conjugate: Characterization, Aggregation, and Adriamycin Release in Vitro, Pharmaceutical Research, May 2002, pp. 681-688, vol. 19, No. 5.
Kun Na et al., Adriamycin loaded pullulan acetate/sulfonamide conjugate nanoparticles responding to tumor pH: pH-dependent cell interaction, internaland cytoxicity in vitro, Journal of Controlled Release, 2003, pp. 3-13, vol. 87.
Kun Na et al., pH-sensitivity and pH-dependent interior structural change of self-assembled hydrogel nanoparticles of pullulan acetate/oligo-sulfonamide conjugate, Journal of Controlled Release, 2004, pp. 513-525, vol. 97.

* cited by examiner

*Primary Examiner*—Michael P. Woodward
*Assistant Examiner*—Eric E. Silverman
(74) *Attorney, Agent, or Firm*—Clayton, Howarth & Cannon, P.C.

(57) ABSTRACT

Drug delivery compositions for specific delivery of a drug to a tumor are described. These compositions include a core for sequestering the drug and a shell to which a ligand is attached for delivery of a drug to target cells. Since normal cells may also be targeted by the ligand, the compositions embed the ligand in the shell until the localized conditions surrounding the tumor cause the ligand to be displayed on the surface of the shell. One composition exhibits shrinkage of the shell at tumor pH, whereas another composition exhibits extension of the ligand at tumor pH. Still another composition causes the ligand to be exhibited at an elevated temperature.

24 Claims, 14 Drawing Sheets

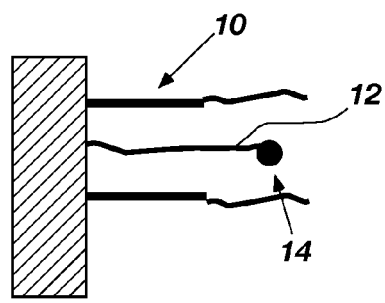
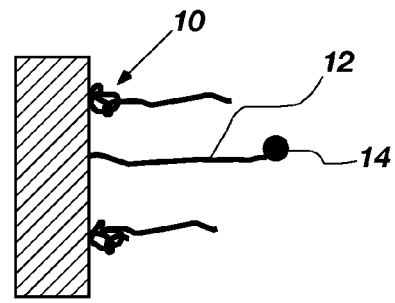
FIG. 1A    FIG. 1B
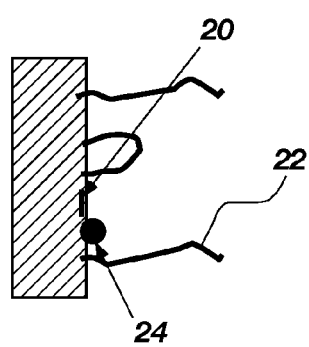
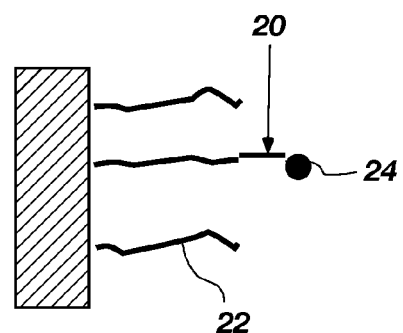
FIG. 2A    FIG. 2B

Folate amination

L-histidine blocking

L-histidine ring-opening polymerization initiated by aminated folate

PLLA/PEG/polyHis-folate block copolymers

*FIG. 8A* pH 7.4 (FITC)
*FIG. 8B* pH 7.4 (ADR)
*FIG. 8C* pH 7.4 (Overlap)
*FIG. 8D* pH 7.2 (FITC)
*FIG. 8E* pH 7.2 (ADR)
*FIG. 8F* pH 7.2 (Overlap)

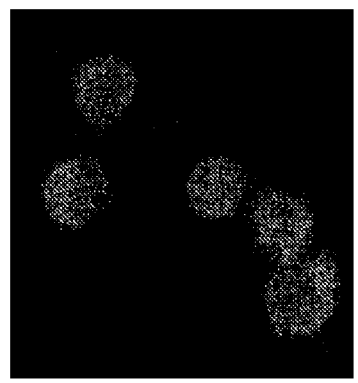
*FIG. 8G* pH 7.0 (FITC)
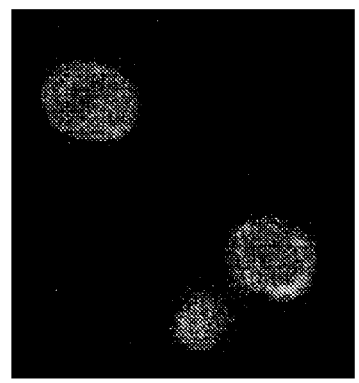
*FIG. 8J* pH 6.8 (FITC)
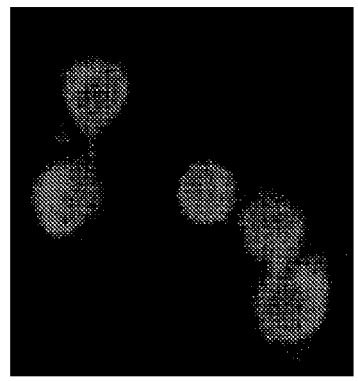
*FIG. 8H* pH 7.0 (ADR)
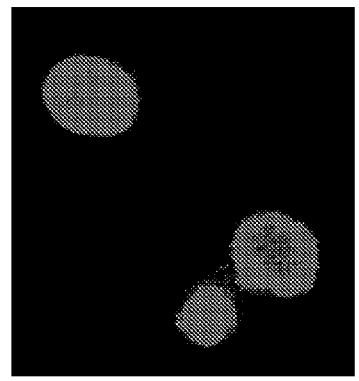
*FIG. 8K* pH 6.8 (ADR)
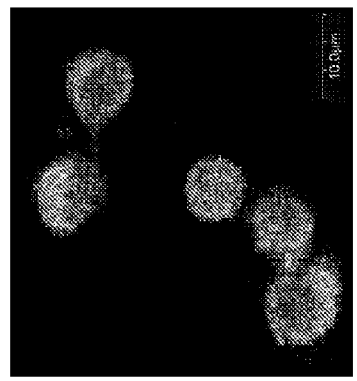
*FIG. 8I* pH 7.0 (Overlap)
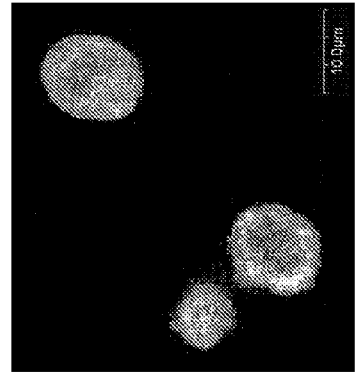
*FIG. 8L* pH 6.8 (Overlap)

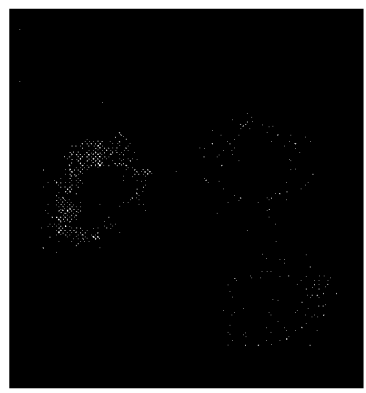
FIG. 9A pH 7.4 (FITC)
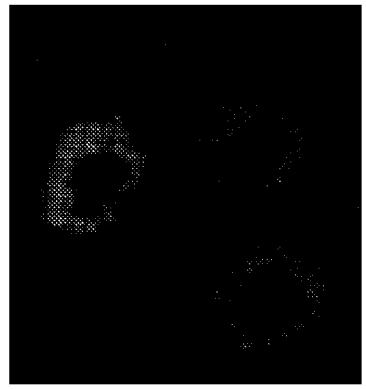
FIG. 9B pH 7.4 (ADR)
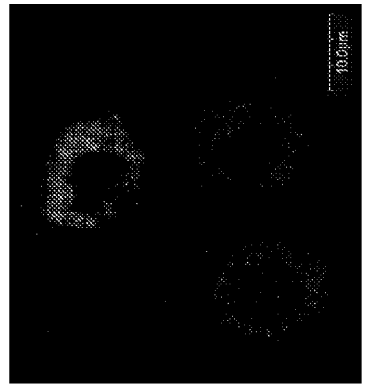
FIG. 9C pH 7.4 (Overlap)
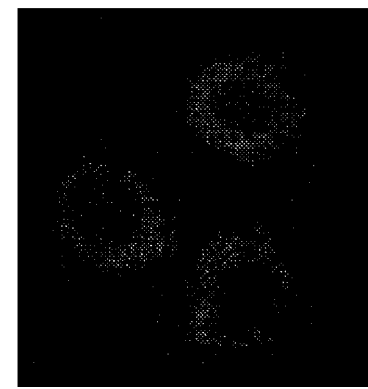
FIG. 9D pH 7.2 (FITC)
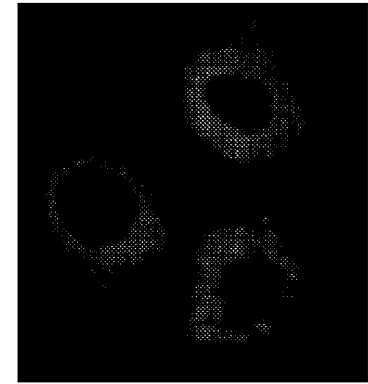
FIG. 9E pH 7.2 (ADR)
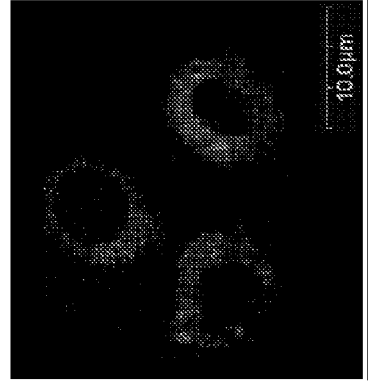
FIG. 9F pH 7.2 (Overlap)

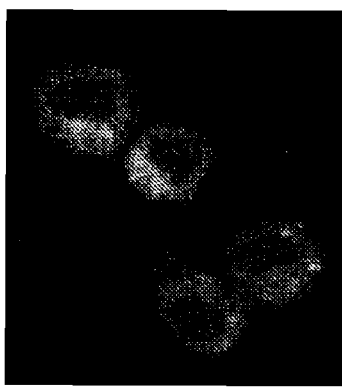
FIG. 9G pH 7.0 (FITC)
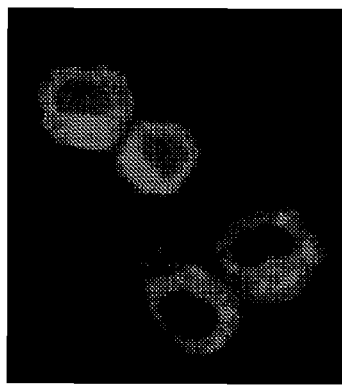
FIG. 9H pH 7.0 (ADR)
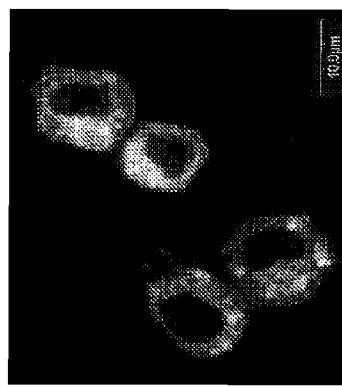
FIG. 9I pH 7.0 (Overlap)
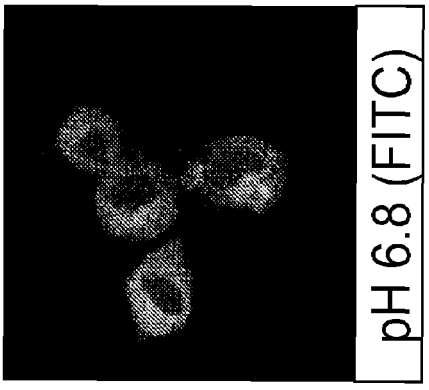
FIG. 9J pH 6.8 (FITC)
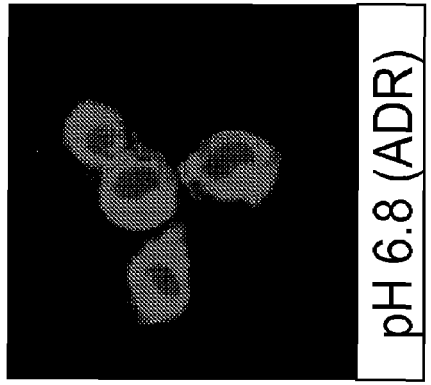
FIG. 9K pH 6.8 (ADR)
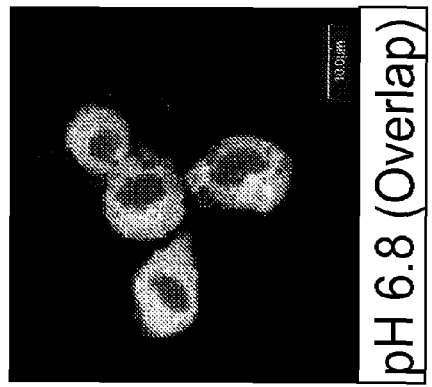
FIG. 9L pH 6.8 (Overlap)

TUMOR ENVIRONMENT-INDUCED LIGAND-EXPRESSING NANOCARRIER SYSTEM

CROSS REFERENCE TO RELATED APPLICATIONS

This application claims the benefit of U.S. Provisional Application No. 60/505,227, filed on Sep. 22, 2003 which is hereby incorporated in its entirety.

STATEMENT REGARDING FEDERALLY SPONSORED RESEARCH OR DEVELOPMENT

Not applicable.

BACKGROUND OF THE INVENTION

This invention relates to drug delivery. More particularly, this invention relates to compositions and methods or delivering drugs to tumor cells.

Cancer cells are often characterized by specific antigens or over-expressed receptors on cell surfaces. Such receptors provide uptake routes for nutrients and signals from the surrounding environment, which nutrients and signals are essential for active growth of the cells. Examples include receptors for folic acid, vitamin B12, and transferrin. S. D. Weitmann et al., Distribution of the folate receptor GP38 in normal and malignant cell lines and tissues, 52 Cancer Res. 3396-3401 (1992); J. F. Ross et al., Differential regulation of folate receptor isoforms in normal and malignant tissues in vivo and in established cell lines. Physiologic and clinical implications, 73 Cancer 2432-2443 (1994); J. Holm et al., High-affinity folate binding in human choroid plexus. Characterization of radioligand binding, immunoreactivity, molecular heterogeneity and hydrophobic domain of the binding protein. 280 Biochem. J. 267-272 (1991).

Active internalization into cells of nutrients, signal molecules, or nanoparticulates via various processes, such as endocytosis and phagocytosis, is a natural consequence of evolution for survival of individual cells, signal transduction pathways, and cellular immune reactions. These processes have now been utilized as an important delivery mode for macromolecular and/or nano-sized carriers, which ferry anticancer drugs, antisense oligonucleotides, genes, or proteins, to tumor cells to kill cells and/or suppress aggressive cell growth. P. S. Low & R. J. Lee, Folate-mediated tumor cell targeting of liposome-entrapped doxorubicin in vitro, 1233 Biochem. Biophys. Acta 134-144 (1995); D. Goren et al., Nuclear delivery of doxorubicin via folate-targeted liposomes with bypass of multidrug-resistance efflux pump, 6 Clinical Cancer Res. 1949-1957 (2000).

Ligand-receptor and antigen-antibody interactions are important modes in active tumor targeting and are frequently utilized for designing carrier systems containing cytostatic agents that minimize undesirable side effects of the drugs. S. P. Vyas et al., Ligand-receptor mediated drug delivery: an emerging paradigm in cellular drug targeting, 18 Critical Review in Therapeutic Drug Carrier System 1-76 (2001).

Before ligand-receptor interactions occur, the anticancer drug carriers should (a) avoid active and massive removal processes in the body, which remove foreign particulates (carriers), and (b) minimize interactions with normal, healthy cells. One approach for accomplishing these requirements is surface decoration of the carriers with hydrophilic polymers, particularly with poly(ethylene glycol) (PEG). Such surface decoration minimizes the adsorption of plasma proteins that mediate particulate uptake (opsonization) by the reticuloendothelium system (RES). This provides a certain degree of stealth effect for particulate carriers, which provides prolonged circulation in the blood stream. Prolonged circulation in the blood stream, in turn, results in a higher probability of the drug reaching tumor sites by the enhanced permeability and retention (EPR) effect in the defective and leaky vasculature in the tumors. M. J. Roberts et al., Chemistry for peptide and protein PEGylation, 54 Adv. Drug Deliv. Rev. 459-476 (2002); G. Molineux, Pegylation: engineering improved pharmaceuticals for enhanced therapy, Cancer Treat Rev. Suppl A:13-16 (2002). The introduction of a ligand to the ends of PEG chains immobilized to the carrier surface is also employed in the design of anticancer carriers for active targeting or internalization.

Receptor-mediated endocytosis has received major attention in the field of drug/gene delivery in the past few decades. This process could be exploited for designing compositions and methods for delivery of site-specific bioactive agents, in particular, for the delivery of anti-cancer agents, because anti-cancer agents have disadvantageous properties, such as nonspecific toxicity, lack of tumor selectivity, and development of multi-drug resistance in various tumor cells. To overcome these problems and to increase the therapeutic index of the drugs, various tumor targeting moieties, such as vitamins, sugars, and antibodies, have been investigated. These target moieties showed to some extent the potential for the effective treatment of tumors. Recently, some kinds of vitamins and sugars have been used as tumor-targeting moieties, because their activities, which can internalize with macromolecules in tumor cells, were confirmed by in vitro tests. However, the successful tumor targeting of carriers with the moieties in vivo has rarely been reported. A reason for this, although tumor targeting combined with receptor-mediated endocytosis is effective, is the same receptors are present on various normal cell surfaces, with various degrees of expression. For instance, even though the receptor of folic acid, a B vitamin, is known to be over-expressed on cancer cells (e.g., ovarian, breast, lung, kidney, and brain tumors), it is also expressed on normal cells because folic acid is an essential nutrient. S. D. Garbis et al., Determination of folates in human plasma using hydrophilic interaction chromatography-tandem mass spectrometry, 73 Anal. Chem. 5358-5364 (2001). Actually, it was reported that the folate binding protein (albumin) was greatly accumulated in liver and kidney compared to controls (albumin without folate) in tumor and non-tumor bearing mouse models, while accumulation in tumor sites was slightly increased. The reason for this observation is unknown, however, two possibilities include: (i) the total amount of folate receptors expressed in liver and kidney is more than that in tumors, even though the folate receptor is over-expressed in tumors, and (ii) the likelihood of folate contacting and binding to liver and kidney is higher than that of contacting and binding to tumors. This reasoning is supported by a report that suggested that liver and kidney are the main organs for folate homeostasis. This means that folate molecules bonded to macromolecules could not serve very well as tumor-targeting moieties in vivo. In particular, in the case of a sugar moiety as a targeting ligand, this phenomenon is extreme. The receptors for sugar moieties such as glucose, galactose, and mannose are distributed at each specific organ. Thus, tumor-site targeting using a sugar moiety is very difficult, because their receptors are also expressed at normal sites. For example, even if the hepatic asialoglycoprotein receptor, found only on hepatocytes (about 500,000 receptor per cell), were a very useful receptor for liver targeting, the targeting of liver tumors using this receptor has been seldom or never reported because the receptor is distributed on all hepatic cells (tumor and normal cells). K. A. Deal et al., Cellular distribution of 111In-LDTPA galactose BSA in normal and Asialoglycoprotein receptor-deficient mouse liver, 25 Nuclear Med. & Biology 379-385 (1998). Thus, active internalization via receptor-mediated endocytosis is not specific in nature to tumor cells and inevitably causes side effects once internalized into normal cells. Therefore, to design a more effective delivery system, the development of a carrier system, which can expose a ligand to specific-site as tumor site, is necessary.

The extracellular pH ($pH_e$) of normal tissues and blood is kept constant at pH 7.4 and pH 7.5, respectively, and their intracellular pH ($pH_i$) is kept constant at pH 7.2. However, in most tumors the pH gradient is reversed ($pH_i$>$pH_e$). Particularly, $pH_e$ is more acidic in tumors than in normal tissues. I. F. Tannock & D. Rotin, Acid pH in tumors and its potential for therapeutic exploitation, 49 Cancer Res. 4373-4384 (1989); S. K. Hobbs et al., Regulation of transport pathways in tumor vessels: Role of tumor type and microenvironment, 95 Proc. Nat'l Acad. Sci. USA 4607-4612 (1998); M. Stubbs et al., Causes and consequences of tumour acidity and implications for treatment, 6 Opinion 15-19 (2000). Although there is variation in in vivo $pH_e$ measurements of human patients having various solid tumors (e.g., adenocarcinoma, squamous cell carcinoma, soft tissue sarcoma, and malignant melanoma) in readily accessible areas (limbs, neck, or chest wall) using needle type microelectrodes, the mean pH value is reported to be 7.06, with a full range of 5.66-7.78. K. Engin et al., Extracellular pH distribution in human tumors, 11 Int. J. Hyperthermia 211-216 (1995). The variation is dependent on tumor histology and tumor volume. Recent measurements of $pH_e$ by noninvasive technology, such as $^{19}F$, $^{31}P$, or $^1H$ probes for magnetic resonance spectroscopy in human tumor xenografts in animals, further verified consistently low $pH_e$. R. van Sluis et al., In vivo imaging of extracellular pH using $^1H$ MRSI, 41 Magn. Reson. Med. 743-750 (1999); A. S. E. Ojugo et al., Measurement of the extracellular pH of solid tumours in mice by magnetic resonance spectroscopy: a comparison of exogenous $^{19}F$ and $^{31}P$ probes, 12 NMR Biomed. 495-504 (1999). All measurements of $pH_e$ of human and animal solid tumors by either invasive or non-invasive methods showed that more than 80% of all measured values falls below pH 7.2. This tumor pH can be further lowered by hyperglycemia. D. B. Leeper et al., Human tumor extracellular pH as a function of blood glucose concentration, 28 Int. J. Radiat. Oncol. Biol. Phys. 935-943 (1994).

The high rate of glycolysis of tumor cells under either aerobic or anaerobic condition has been thought to be a major cause of low $pH_e$. The tumor cells synthesize ATP by both mitochondrial oxidative phosphorylation and glycolysis. Glycolysis produces two moles of lactic acids ($pK_a$=3.9) and two moles of ATP by consuming one mole of glucose. Hydrolysis of ATP also produces protons. Despite the high production rate of protons in tumor cells, their cytosolic pH, particularly of resistant cells, remains alkaline, which is favorable for glycolysis, by exporting protons out of the cells by unknown mechanisms. This leads to low $pH_e$ with the help of inadequate blood supply, poor lymphatic drainage, and high interstitial pressure in tumor tissues. I. F. Tannock & D. Rotin, supra; S. K. Hobbs et al., supra; M. Stubbs et al., supra. However, it is of interest to note that glycolysis-deficient variant cells (lacking lactate dehydrogenase) produced negligible quantities of lactic acid but still presented an acidic environment. M. Yamagata et al., The contribution of lactic acid to acidification of tumours: studies of variant cells lacking lactate dehydrogenase, 77 Br. J. Cancer 1726-1731 (1998). This finding has been interpreted as meaning that acidity is a phenotype of tumor cells rather than a consequence of cell metabolic events. The acidic environment may benefit the cancer cells, because it promotes invasiveness (metastasis) by destroying the extracellular matrix of surrounding normal tissues.

This tumor $pH_e$ can be further manipulated to shift to even lower pH by administration of glucose. The rate of glucose uptake by tumor cells is higher than that of normal cell due to higher metabolism and greater production and secretion of lactic acid. This can lead to lower pH of the extracellular matrix and can be beneficial for the approaches described in this application.

In view of the foregoing, it will be appreciated that providing a tumor-selective targeting system for drug delivery would be a significant advancement in the art.

BRIEF SUMMARY OF THE INVENTION

A feature of an illustrative embodiment of the invention is to provide a tumor-selective targeting system for drug delivery wherein internalization of the drug occurs only in tumor cells and not in normal cells.

A feature of another illustrative embodiment of the invention is to provide a tumor-targeting drug delivery system wherein an interacting ligand is buried in the surface hydrophilic shell of core-shell type polymeric micelles, thus minimizing the interactions with normal cells or tissues during circulation while the ligands are exposed on the surface of the outer shell of the carriers only when the carriers arrive at the tumor sites.

Still another feature of an illustrative embodiment of the present invention is to provide a tumor-targeting drug delivery system that interacts with tumor cells and causes receptor-mediated endocytosis.

Yet another feature of an illustrative embodiment of the invention is to provide polymeric nano-carriers that can express the interacting ligand by lowering pH or increasing temperature from normal blood to tumor site.

These and other features and advantages are addressed by providing a drug delivery composition comprising (a) a mixed polymeric micelle comprising an inner core and an outer shell, wherein the mixed polymeric micelle comprises a mixture of (i) a first amphiphilic block copolymer comprising a ligand covalently bonded thereto and (ii) a second amphiphilic block copolymer comprising a biodegradable, pH-sensitive polymer block that comprises a globular configuration at less than about pH 7.0 and comprises an extended configuration at pH 7.4 or greater; and (b) a drug disposed in the inner core.

Another illustrative embodiment of the invention comprises a drug delivery composition comprising (a) a mixed polymeric micelle comprising an inner core and an outer shell, wherein the mixed polymeric micelle comprises a mixture of (i) an amphiphilic block copolymer and (ii) a pH-sensitive block copolymer having a ligand covalently bonded thereto, wherein the pH-sensitive block copolymer comprises an extended configuration at less than about pH 7.0 and a globular configuration at about pH 7.4 or greater; and (b) a drug disposed in the inner core.

Still another illustrative embodiment of the invention comprises a drug delivery composition comprising (a) a mixed polymeric micelle comprising an inner core and an outer shell, wherein the mixed polymeric micelle comprises a mixture of (i) an amphiphilic block copolymer and (ii) a temperature-sensitive block copolymer having a ligand covalently bonded thereto, wherein the temperature-sensitive block copolymer comprises an globular configuration at 37° C. and an extended configuration at about 38° C. to about 45° C.; and (b) a drug disposed in the inner core.

Yet another illustrative embodiment of the invention comprises a drug delivery composition comprising (a) a mixed polymeric micelle comprising an inner core and an outer shell, wherein the mixed polymeric micelle comprises a mixture of (i) an amphiphilic block copolymer and (ii) a temperature-sensitive block copolymer having a ligand covalently bonded thereto, wherein the temperature-sensitive block copolymer comprises an extended configuration at 37° C. and a globular configuration at about 38° C. to about 45° C.; and (b) a drug disposed in the inner core.

BRIEF DESCRIPTION OF THE SEVERAL VIEWS OF THE DRAWINGS

FIGS. 1A-B show a schematic representation of shrinking of the outer shell of the drug delivery micelle system, according to an illustrative embodiment of the present invention, to expose the tumor-targeting ligand at tumor pH.

FIGS. 2A-B show a schematic representation of extension of the tumor-targeting ligand in the outer shell of the drug delivery micelle system, according to an illustrative embodiment of the present invention, to effect exposure of the ligand at tumor pH.

FIGS. 8A-L show confocal microscopy analysis of biotinylated Carrier 4 mixed micelles (ADR-loaded at a concentration of 0.5 μg/mL) with conjugation of FITC, exposed to MCf-7/ADR$^R$ cells (1×10$^5$ cells) for 30 min. FIGS. 8A-C show fluorescence at pH 7.4 of FITC, ADR, and both FITC and ADR, respectively. FIGS. 8D-F show fluorescence at pH 7.2 of FITC, ADR, and both FITC and ADR, respectively. FIGS. 8G-I show fluorescence at pH 7.0 of FITC, ADR, and both FITC and ADR, respectively. FIGS. 8J-L show fluorescence at pH 6.8 of FITC, ADR, and both FITC and ADR, respectively.

FIGS. 9A-L show confocal microscopy analysis of biotinylated Carrier 5 mixed micelles (ADR-loaded at a concentration of 1 μg/mL) with conjugation of FITC, exposed to MCf-7/ADRR cells (1×10$^5$ cells) for 30 min. FIGS. 9A-C show fluorescence at pH 7.4 of FITC, ADR, and both FITC and ADR, respectively. FIGS. 9D-F show fluorescence at pH 7.2 of FITC, ADR, and both FITC and ADR, respectively. FIGS. 9G-I show fluorescence at pH 7.0 of FITC, ADR, and both FITC and ADR, respectively. FIGS. 9J-L show fluorescence at pH 6.8 of FITC, ADR, and both FITC and ADR, respectively.

DETAILED DESCRIPTION

Figure 3A:
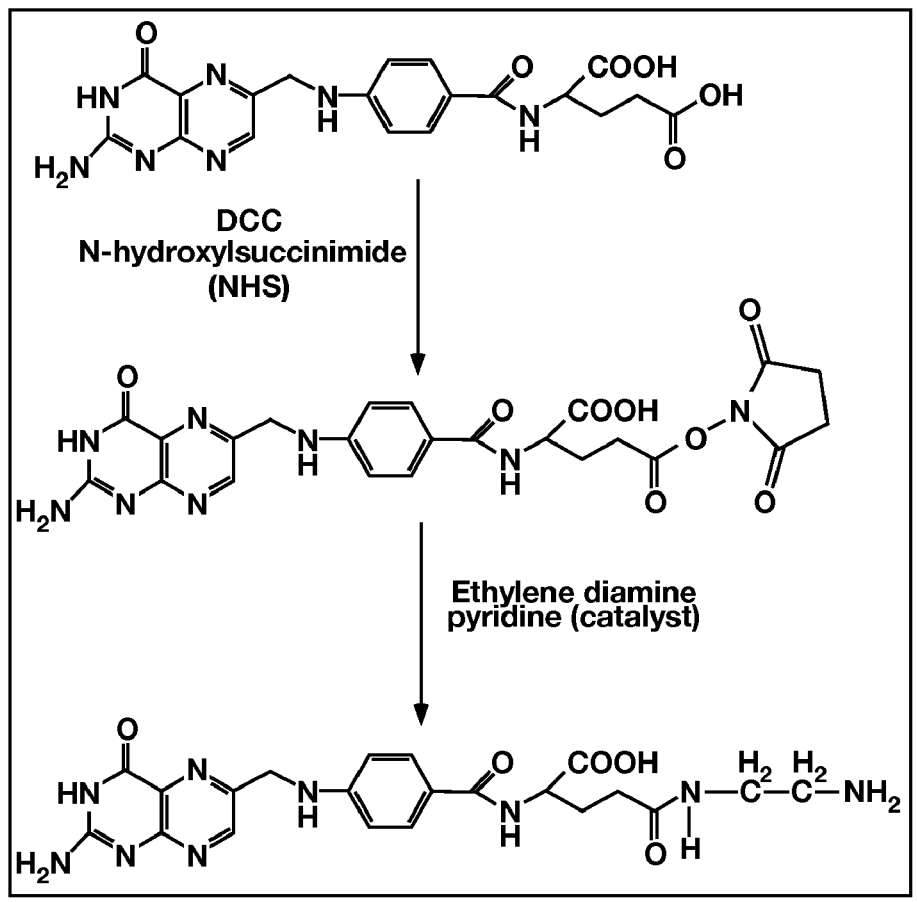
FIG. 3A shows a synthetic scheme for folate amination.

Before the present tumor-targeting drug deliver compositions and methods are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to a mixed polymeric micelle containing "a drug" includes a mixture of two or more drugs, reference to "an amphiphilic copolymer" includes reference to one or more of such amphiphilic copolymers, and reference to "a ligand" includes reference to two or more of such ligands.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "FITC" means fluorescein isothiocyanate, and "ADR" or "DOX" means adriamycin or doxorubicin.

To reduce or minimize undesired interactions or undesired uptake into normal sites, a biodegradable nanocarrier has been developed wherein access to the ligand is controlled by lowering pH and increasing temperature. In this embodiment, the ligand is hidden in a hydrophilic shell of a core-shell nanostructure during circulation in the blood. The hidden or shielded ligand is exposed on the surface of the nanocarrier for interaction with tumor cells and internalization in tumor cells once the carriers reach the tumor sites via extravasation through leaky tumor vessels. The nanoparticle comprises (a) an amphiphilic block copolymer without a ligand, and (b) another amphiphilic block copolymer with a ligand attached to a tumor-pH-recognizing polymer. This nanoparticle was designed and prepared for targeting a pH as close to 7.2 as possible, so that the carrier can be used for targeting a broad range of solid tumors. The nanoparticle is configured for distinguishing differences in pH as small as 0.2 pH units.

Ligands or targeting moieties that can be used according to the present invention include all types of ligands that are internalized via receptor-mediated endocytosis. Categories of such ligands include vitamins, monoclonal antibodies, tumor necrosis factor-related apoptosis including ligand (TRAIL), endogenous ligands, immunological ligands, glycoconjugates, organ specific ligands, and the like.

Illustrative vitamins according to the present invention include folate, biotin, retinoic acid, thiamine, niacin, riboflavin, pantothenic acid, pyroxidine, and the like.

Illustrative monoclonal antibodies according to the present invention include monoclonal antibodies specific to Fc, Fab', or complement; anti-idiotype or anti-anti-idiotype monoclonal antibodies against tumor epitopes; bispecific antibodies and antibody-enzyme conjugates; haptens; Fab' or F(ab)$_2$ fragments; single-chain Fv fragments (scFv); immunotoxins and chimeric toxins; Fab' fragments of the monoclonal antibody Mu-9 (colon-specific antigen p(CSAp)); PK4S sheep anti-CEA (carcino embryonic antigen); human milk fat globule 1 (HMFG1; polymorphic epithelial mucin (PEM, epithelial ovarian tumor)); OC 125 (tumor specific cell-surface antigen CA-125, ovarian cancer; tumor vascular endothelium monoclonal antibody (TES-23)); KMT-17, fibrosarcoma; A2B5, CDO9, and IC2 (monoclonal antibodies that specifically bind to beta cells in the pancreas).

Illustrative endogenous ligands that can be used according to the present invention include transferrin, folate, lipoprotein, epidermal growth factor, nerve growth factor, insulin, α-fetoprotein, macroglobulin, and the like.

Illustrative immunological ligands that can be used according to the present invention include recombinant CD molecules, CD4/rCD4-toxin conjugate, major histocompatibility complex (MHC) peptides, interleukins, interferons, ECM ligands including RGD and ISGR, synthetic sLe$^x$ or sLE$^a$ analogs, recombinant gp120 and gp41, and the like.

Illustrative glycoconjugates that can be used according to the present invention include lectins, glycolipids, asialoglycoprotein, neoglycoprotein, glycosides, viroproteins, polysaccharides, lipopolysaccharides, glucose or derivatives thereof, galactose or derivatives thereof, maltose or derivatives thereof, mannose or derivatives thereof, and the like.

Illustrative organ-specific ligands that can be used according to the present invention include liver-targeting moieties, such as N-acetylgalactoseamine, β-galactose, α-galactose, lactose, glucose, mannose, fibronectin, α2-macroglobulin, Fc (immune complexes, opsonized particle), Cb3 (complement factors), fucose, insulin (insulin receptor), epidermal growth factor, IgA, transferrin, low density lipoprotein (LDL), high density lipoprotein (HDL), glycyrrhizin, glucose residues, lactoseaminated ferritin (Lac-Fer), lactobionic acid, biotin, negatively charged proteins, sulfated polysaccharides (e.g., chondroitin sulfate, heparin), and the like; lung-targeting moieties, such as antagonist G; pancreas-targeting moieties, such as sulfonylurea, GLP-1, somatostatin, glutamic acid decarboxylase, carboxypeptidase H, GM2-1 pancreatic islet ganglioside, ICA 69 autoantigen, imogen 38, and the like; estrogen receptor positive tumors, such as cyclopentadienyl tricarbonyl metal complex and the like.

Drugs that can be delivered using the drug delivery compositions of the present invention include adriamycin or doxorubicin, paclitaxel, 5-fluorouracil (5-FU), vinblastine sulfate, daunorubicin, mitoxantrone, idarubicin, etoposide, teniposide, vincristine, vinblastine, dactinomycin, valinomycin, puromycin, mithramycin, colchicine, mitomycin-C, trimetrexate, actinomycin-D, cyclophosphamide, mechlorethamine, ifosphamide, camustine (BCNU), semustine (CCNU), cytarabine (Ara-C), methotrexate, cisplatin, carboplatin, bleomycin, hydroxyurea, and the like.

Other bioactive agents that can be delivered according to the present invention include proteins, such as interferon-α (IFN-α), interferon-γ (IFN-γ), aldesleukin (IL-2), atriopeptin III, cyclosporin A, insulin, ovalbumin, LHRH, somatostatin, thyrotropin, t-PA, sargramostim (CSF-GM), antithrombin III, calcitonin, erythropoietin, and the like; peptides, such as growth factor, GLP-1, and the like; nucleic acids, such as nucleic acids that encode therapeutic agents, antisense agents, and the like; toxins; and the like.

Numerous polymers can be used according to the present invention for making of pH-sensitive micelles. For example, amphiphilic polymers that can be used according to the present invention include amphiphilic polymers, such as poly(ethylene oxide)-poly(propylene oxide)-poly(ethylene oxide) triblock copolymers, such as the PLURONIC™ block copolymers.

Biodegradable polymer blocks that can be used for making copolymers include poly(L-lactic acid) (PLLA), poly(lactide-co-glycolide) (PGLA), poly(glycolic acid) (PGA), polyorthoester, polyanhydride, poly(histidine) (polyHis) and polyHis copolymers.

Non-biodegradable polymer blocks that can be used for making copolymers include poly(alkylcyanoacrylate), poly(ethylcyanoacrylate), poly(isohexylcyanoacrylate), and derivatives thereof.

Further, pH-sensitive polymers that can be used for attachment to a ligand include poly(histidine) (poly(His)) and poly(His) copolymers. Comonomers that can be used with L-histidine for making poly(His) copolymers include leucine, alanine, phenylalanine, and the like.

Still further, pH-sensitive polymers that can be used in the outer shell include polymers containing poly(sulfonamide) groups and copolymers thereof, and poly(His) and poly(His) copolymers. Comonomers that can be used with L-histidine for making poly(His) copolymers include leucine, alanine, phenylalanine, and the like.

Temperature sensitive polymers for use in the outer shell for making temperature sensitive micelles include poly(N-isopropylacrylamide) and its copolymers, and PEG/PLLA triblock or multiblock copolymers.

Poly(His) and its copolymers should generally be used in the molecular weight range of about 300 to about 80,000. Such polymers in the range of about 600 to about 10,000 are illustrative. PEG blocks should generally be used in the molecular weight range of about 300 to about 20,000. Such polymers in the range of about 1000 to about 10,000 are illustrative. The total molecular weight of block copolymers used according to the present invention should generally be in the molecular weight range of about 600 to about 100,000; and illustratively in the range of about 2000 to about 20,000.

Types of block copolymers that are used as pH-sensitive polymers with a ligand attached thereto include ligand/AB-type block copolymers, such as ligand-poly(His)-PLLA and ligand-poly(His)-PLGA; ligand/ABA-type block copolymers, such as ligand-poly(His)-PEG-poly(His); ligand/BAC-type block copolymers, such as ligand-PEG-poly(His)-PLLA and ligand-PEG-poly(His)-PLGA; ligand/BABA-type block copolymers, such as ligand-PEG-poly(His)-PEG-poly(His); ligand/BABC-type block copolymers, such as ligand-PEG-poly(His)-PEG-PLLA and ligand-PEG-poly(His)-PEG-PLGA; and the like.

Block copolymers that can be used in the outer shell of the pH-sensitive micelles include AB-type block copolymers, such as PEG-poly(His), PEG-PLLA, PEG-PLGA, poly(sulfonamide)-PLLA, and poly(sulfonamide)-PLGA; ABC-type block copolymers, such as PEG-poly(sulfonamide)-PLLA and PEG-poly(sulfonamide)-PLGA; ABA-type block copolymers, such as PEG-PLLA-PEG; BAB-type block copolymers, such as PLLA-PEG-PLLA; $(AB)_n$-type alternating multiblock copolymers, such as (poly(sulfonamide)-PEG)$_n$ random multiblock copolymers; and the like.

A first illustrative embodiment of the invention is a ligand-exposing system comprising an outer shell that if configured for shrinking at tumor pH (e.g., using a sulfonamide-based biodegradable polymer). This micelle system has a ligand that can be exposed by the shrinking of pH-sensitive outer shell at tumor pH. FIGS. 1A-B show a schematic representation of a portion of a micelle comprising a pH-sensitive outer shell made up of a pH-sensitive polymer 10 and a ligand-bearing polymer 12. At pH 7.4-7.5, such as is encountered in normal tissues and the bloodstream, the pH-sensitive polymer 10 is in an extended configuration such that is shields or hides the ligand 14 (FIG. 1A). At tumor pH, the pH-sensitive polymer 10 contracts or shrinks, thus exposing the ligand 14 on the surface of the micelle and leaving the ligand 14 available for interaction with cell surface receptors and the like. Thus, the ligand in this system cannot interact to its receptor at normal pH because it is covered with the hydrophilic outer shell. However, at tumor pH it can easily interact and internalize via endocytosis due to the outer shell shrinking or contracting.

For example, this system can be prepared by the mixing of two different amphiphilic block copolymers: one is ligand/PEG (3.4K)/PLLA (3K), the other is PEG (2K)/Biodegradable pH-sensitive polymer (3K)/PEG (2K)/PLLA (3K). The development of biodegradable pH-sensitive polymer responsive to tumor pH is a rate-determining step in this system because extracellular tumor pH (<7.0) is slightly lower than the normal pH (7.4). To prepare an outer shell that shrinks or contracts at tumor pH, a sulfonamide group is used. "Sulfonamide" is used herein to refer to derivatives of para-aminobenzene sulfonamide (sulfanilamide). It is a weak acid because the hydrogen atom of the amide nitrogen ($N^1$) can be readily ionized to liberate a proton in solution. By introducing a selected sulfonamide group into water soluble polymers, a new class of pH sensitive polymers has been synthesized. These polymers demonstrate a first-order-like transition in solubility and swelling by pH. Selecting an appropriate sulfonamide or changing the polymer composition tailors this transition pH to selected conditions. For examples, a selected, representative sulfonamide of 4-amino-N-[4,6-dimethyl-2-pyrimidinyl]benzene sulfonamide (sulfamethazine; CAS No. 57-68-1) with its known pKa of 7.4, was modified with methacryloyl chloride to produce a polymerizable sulfonamide monomer. Unlike conventional pH-sensitive polymers, this copolymer of the sulfonamide monomer and N,N-dimethylacrylamide demonstrated a reversible first-order like transition in solubility by pH. By varying the type of sulfonamide and the copolymer composition, a broad range of the transition pH can be targeted. Also, to utilize the pH-responsive property of sulfonamides in targeting tumor $pH_e$, a new class of pH-responsive polymers was synthesized by conjugating a sulfonamide, sulfadimethoxine (SDM; CAS No. 122-11-2), to succinylated pullulan acetate (PA). The polymers formed self-assembled PA/SDM hydrogel nanoparticles in aqueous media, which was confirmed by fluorometry and field emission-scanning electron microscopy. The nanoparticles showed good stability at pH 7.4, but shrank and aggregated below pH 7.0 due to the sulfonamide's property of switching of from hydrophilic to hydrophobic. The DOX release rate from the PA/SDM nanoparticles was pH-dependent and significantly enhanced below pH 6.8. Furthermore, a sulfonamide homopolymer was synthesized by radical polymerization of a vinylated SD (SD monomer; SDM) using 2-aminoethanethiol as a chain transfer agent to enhance the pH-sensitivity. For the preparation of pH-sensitive polymeric micelle, the polymer was coupled to a carboxylic PEG (Mw=2,000)/PLLA (Mw=3,500) block copolymer. The micelle showed an aggregation behavior below pH 7.0 due to the presence of deionized SDM on the surface, while the other micelles were stable. The polymeric micelle sharply responded to the change in pH around the physiological pH.

An illustrative variation of this embodiment of the invention comprises a biodegradable polymer based on sulfonamide. To create a biodegradable sulfonamide polymer at a middle position of a block copolymer, a poly(amino acid-grafted-sulfonamide) is synthesized and then conjugated to aminated PEG. The resulting PEG/poly(amino acid-grafted-sulfonamide) copolymer is then coupled to carboxylic PEG/PLLA block copolymer to result in PEG/poly(amino acid-grafted-sulfonamide)/PEG/PLLA. Micelles that expose the ligand at tumor pH are then prepared by the mixing of PEG/poly(amino acid-grafted-sulfonamide)/PEG/PLLA and ligand/PEG/PLLA block copolymer.

A second illustrative embodiment of the invention comprises a ligand expansion system, wherein the ligand is shielded or hidden at normal pH, but exposed at tumor pH. This embodiment comprises a mixed micelle comprising (a) a pH-sensitive block copolymer with an attached ligand, and (b) an amphiphilic block copolymer. FIGS. 2A-B a schematic representation of a portion of a micelle comprising a pH-sensitive outer shell. The outer shell comprises a pH-sensitive, ligand-bearing polymer 20 and a second polymer 22. At normal pH, the ligand 24 is shielded or hidden by the second polymer 22 of the outer shell (FIG. 2A), because the ligand-bearing polymer 20 is in a compact configuration. At tumor pH, however, the ligand-bearing polymer 20 is in an extended or expanded configuration (FIG. 2B), thus exposing the ligand such that it can interact with receptors and the like on the cell surface of tumors. Thus, even though the ligand will be hidden at normal pH, it will be accessible at extracellular tumor pH, because the pH-sensitive portion in the polymer can be switched from hydrophobic (at normal pH) to hydrophilic one (at extracellular tumor pH). To endow pH-sensitivity to the ligand-bearing polymer, a poly (L-histidine) block is used. L-Histidine is a basic amino acid with a pK of 6.5. This pK value is influenced by the polymerization of histidine, comonomer, and microenvironment. The imidazole ring in L-histidine has a lone pair of electrons on the unsaturated nitrogen, which endows an amphoteric nature to poly(L-histidine) (polyHis). PolyHis is protonated at pH 5.0-7.0, being influenced by the molecular weight of poly(L-histidine). PolyHis with a molecular weight of >10,000 was reported to be soluble only below pH 6.0 by protonation.

Poly(L-histidine) was synthesized using an aminated ligand as an initiator. The polymer was coupled to PEG/PLLA block copolymer. The extended ligand system is easily made by mixing of PEG/PLLA and ligand/poly(L-histidine)/PEG/PLLA block copolymers.

EXAMPLE 1

To demonstrate the invention, two vitamins (folate and biotin) were selected as ligands, and several micelle systems were prepared, as described below.

Carrier 1 comprised poly(His5K)/PEG2K block copolymer and PLLA3K/PEG2K (60:40 wt %) as a mixed micelle control. Such micelles had an average diameter of about 100 nm.

Carrier 2 comprised poly(His5K)/PEG2K and PLLA3K/PEG2K-folate (60:40 wt %) as a mixed micelle. Such micelles also had an average diameter of about 100 nm.

Carrier 3 comprised poly(His5K)/PEG2K and PLLA3K/PEG2K-poly(His1K)-folate (60:40 wt %) as a mixed micelle. Such micelles also had an average diameter of about 100 nm.

Carrier 4 comprised poly(His5K)/PEG2K and PLLA3K/PEG2K-poly(His1K)-biotin (60:40 wt %) as a mixed micelle. Such micelles also had an average diameter of about 100 nm.

Carrier 5 comprised PLLA3K/PEG2K and PLLA3K/PEG2K-poly(His1K)-biotin.

Synthesis of folate-poly(L-histidine)-PEG-PLLA

Figure 3B:
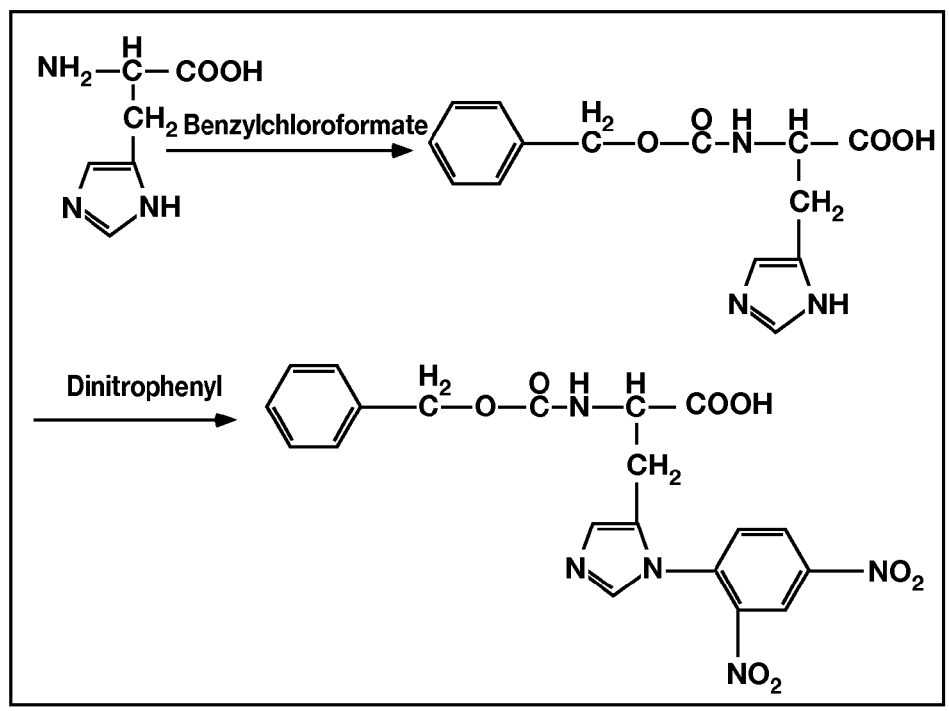
FIG. 3B shows a synthetic scheme for L-histidine blocking.
Figure 3C:
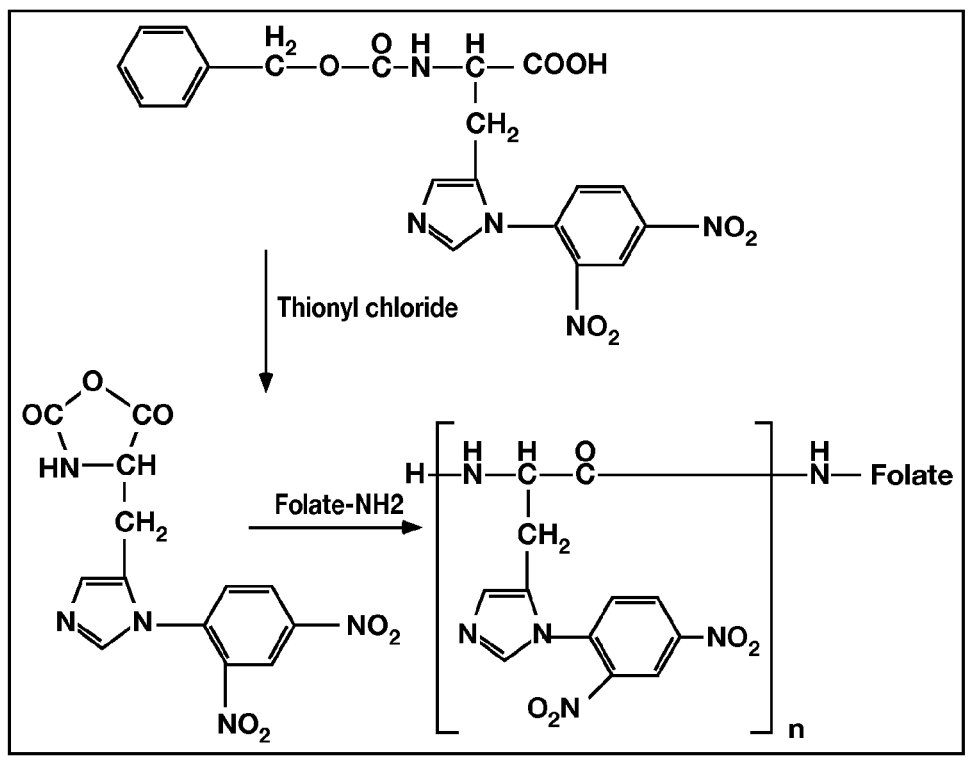
FIG. 3C shows a synthetic scheme for L-histidine ring-opening polymerization initiated by aminated folate.
Figure 3D:
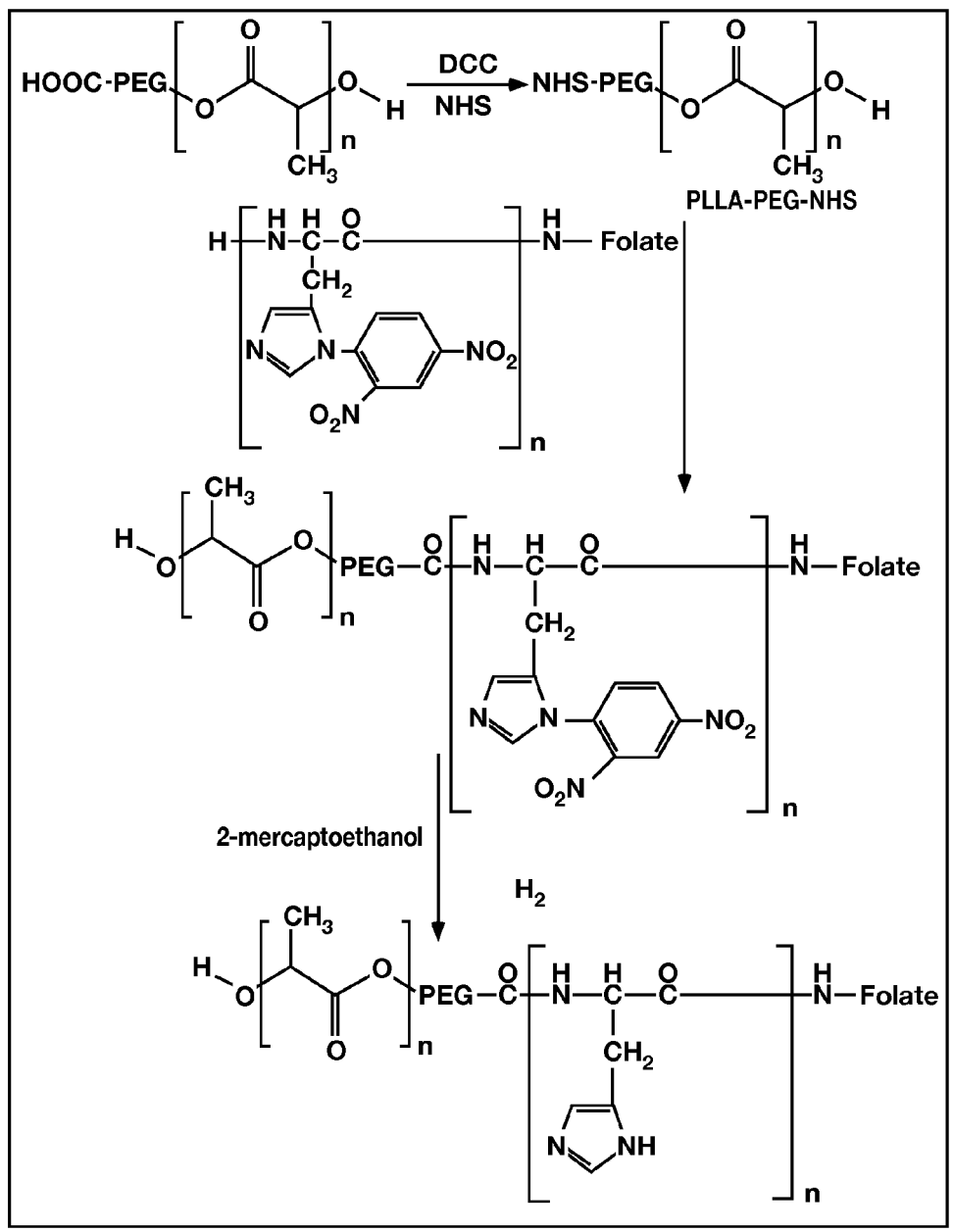
FIG. 3D shows a synthetic scheme for PLLA/PEG/polyHis-folate block.

Histidine-NCA was synthesized using thionyl chloride after the amine protection steps with benzylchoroformate and 2,4-nitrofluorobenzene, according to the procedure of U.S. patent application Ser. No. 10/846,487, and E. S. Lee et al., Polymeric micelle for tumor pH and folate mediated targeting, 91 J. Control. Release 103-113 (2003), both of which are hereby incorporated by reference. To synthesize PLLA-PEG-poly(L-histidine)-folate, amine protected histidine-NCA (30 mmol; FIG. 3B) was dissolved in DMF (30 mL) in the presence of aminated folate (1 mmol; FIG. 3A) as an initiator and reacted for 3 days at room temperature. After reaction, diethyl ether was added to the solution for precipitation of reactant. The preactivated PLLA-PEG-COOH with NHS was added in same mole ratio to poly($^{im}$DNP-L-histidine)-folate (FIG. 3C) in THF. The reaction was carried out for 2 days, and then the product was collected by precipitation after adding excess n-hexane. The product was then dialysed (Spectra/Por; MW cut off 6,000) to remove unreacted ingredients. The product was then freeze-dried. To remove the DNP group, the polymer was dissolved in dimethylformamide (DMF) and then 2-mercaptoethanol was added (40-fold mole ratio excess) to DMF with TEA (1 drop) (FIG. 3D). DMF/diethyl ether recrystallization was twice repeated to remove 2-mercaptoethanol.

Cell Experiment with Sensitive MCF-7

Figure 4B:
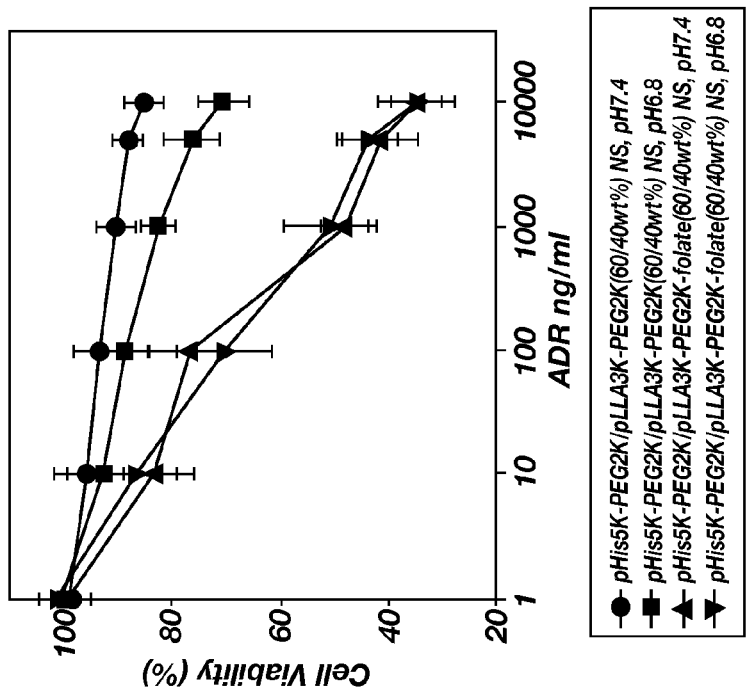
FIG. 4B shows cell viability as a function of ADR concentration when delivered with Carrier 1 at pH 7.4 (●) and at pH 6.8 (■) and with Carrier 2 at pH 7.4 (▲) and at pH 6.8 (▼)
Figure 4A:
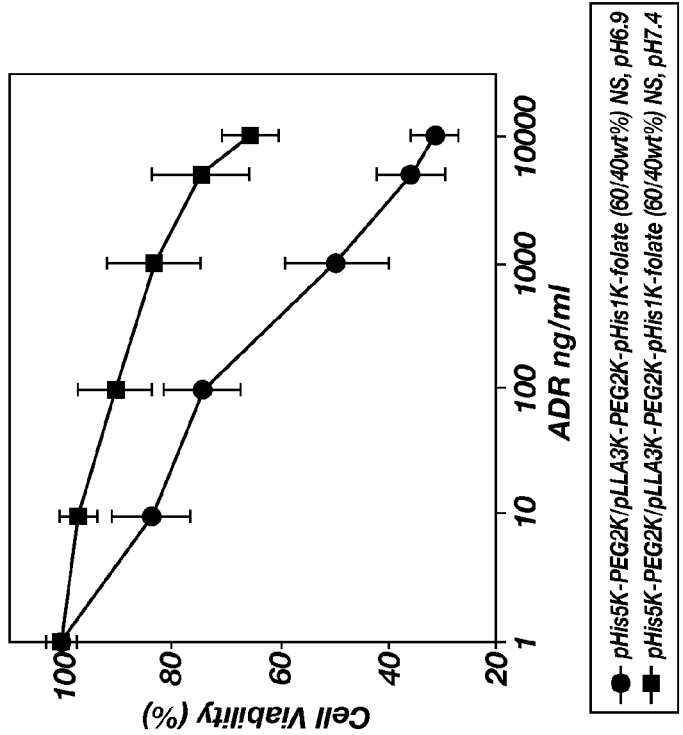
FIG. 4A shows cell viability as a function of adriamycin (ADR) concentration when delivered with Carrier 3 at pH 6.8 (●) and at pH 7.4 (■).

Mixed polymeric micelles of folate-poly(L-histidine)-PEG-PLLA and PolyHis-PEG were formed by the dialysis method. The mixed polymeric micelles showed higher cell cytotoxicity at tumor pH than at normal pH (FIGS. 4A-B). This result indicates that interaction with and internalization of the micelles into a selected breast tumor cell line of MCF-7 increased as pH decreased.

Biotin/polyHis/PEG/PLLA

Figure 5A:
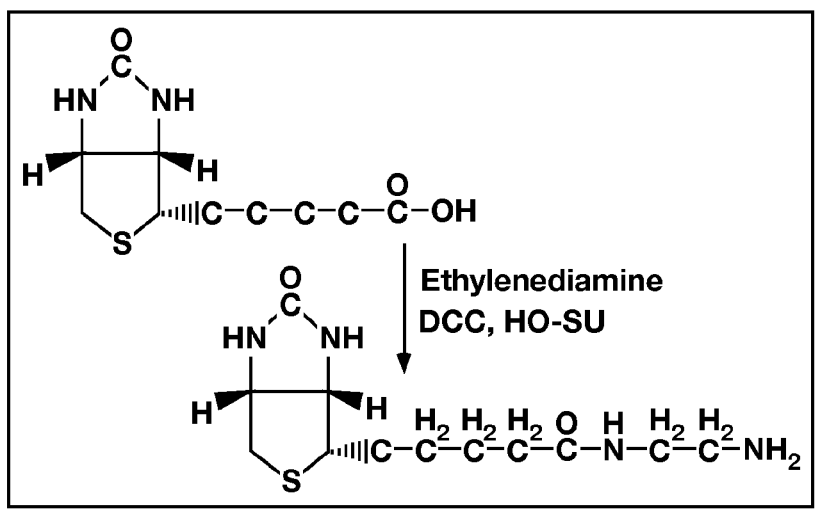
FIG. 5A shows a synthetic scheme for biotinamination.
Figure 5B:
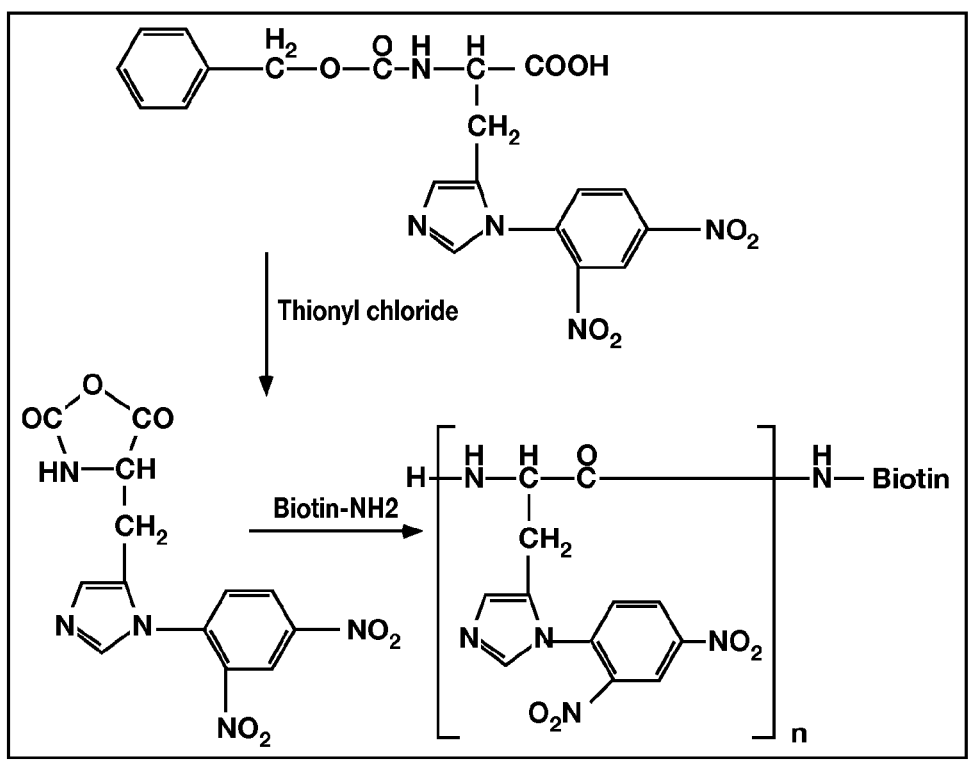
FIG. 5B shows a scheme for synthesis of biotin-polyHis.

For the amination of biotin (FIG. 5A), biotin (1 mmol) was activated with DCC (1.25 mmol) and NHS (1.5 mmol) in DMF. Biotin-NHS was collected after recrystallization (DMF/diethyl ether). Biotin-NHS (1 mmol) was dissolved in DMF and then mixed with ethylene diamine (20 mmol) plus 500 µg pyridine and allowed to react at room temperature overnight. The reaction was confirmed by thin layer chromatograph (TLC) analysis (silica gel plate, 2-propanol/chloroform=70/30 vol %). The product was dissolved in 1 N NaOH and then biotin-amine was precipitated and collected by filtration. The product was also dissolved in 2 N HCl and then filtered to remove insoluble materials. The solution was freeze-dried for 3 days. For preparation of salt-detached biotin-amine, biotin-amine was mixed with one drop of TEA and recrystallized by adding excess diethyl ether. Incorporation into block copolymers was carried out as described above and as summarized in FIG. 5B.

pH-Dependent Aggregation of Carrier 4 Interaction with Avidin

Figure 6:
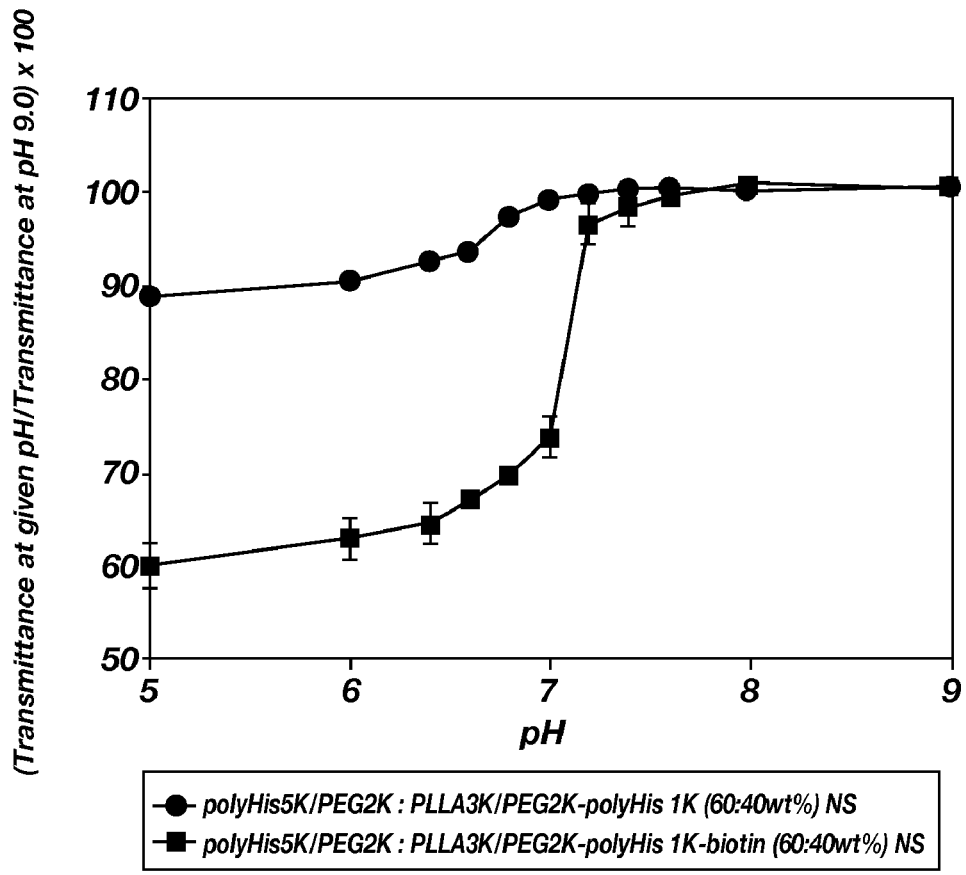
FIG. 6 shows changes in turbidity of Carrier 1 (●) and Carrier 4 (■) on decreasing pH; each polymeric micelle sample (1.0 g/L) was mixed with avidin (0.1 g/L); transmittance of each polymeric micelle sample was measured at 24 hours and determined at 500 nm and was baseline-corrected with 0.1 g/L avidin at each pH (n=3).

The aggregation behavior of Carrier 4 by interaction with avidin in solution was studied using turbidity change at various pHs (FIG. 6). Avidin has four binding sites and a high binding affinity for biotin. On decreasing the pH from 7.2 to 6.0, turbidity changed slightly for Carrier 1, however, a significant change was observed for Carrier 4. This change of turbidity was attributed to the aggregation of nanoparticles by the interactions between avidin and biotin, which was exposed at the nanoparticle's surface due to deprotonization of the poly(His) attached to the biotin moiety. When Carrier 4 was prepared at pH 8.0, the outer shell was composed of PEG. Thus, such carrier showed high stability above pH 7.4. However, below pH 7.0 the protonized poly(His)1K led to exposing of the biotin ligand, resulting accessibility for interaction with avidin.

Flow Cytometry Analysis of Carrier 4 at pH 7.2 and 7.0

Figure 7:
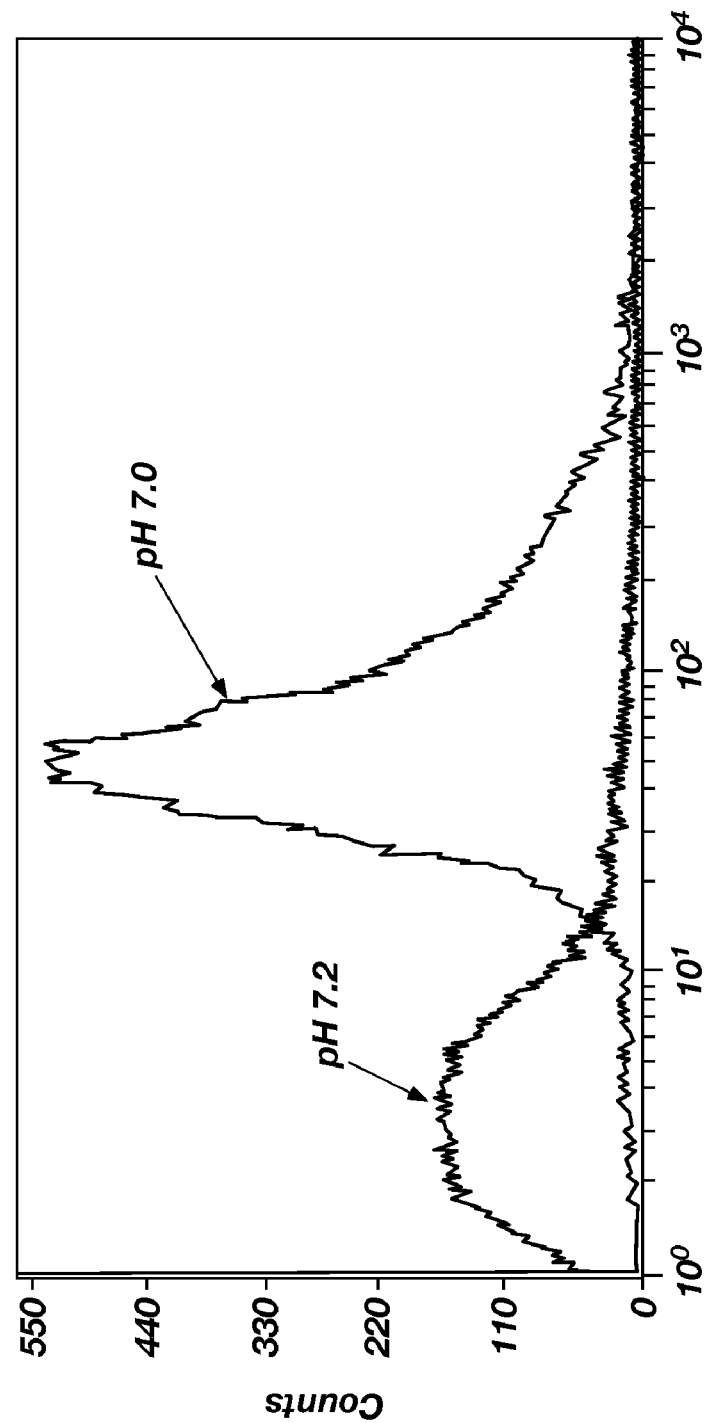
FIG. 7 shows flow cytometry analysis with Carrier 4 (5 μg/mL) exposed to MCf-7/ADR$^R$ cells (1×10$^5$ cells) for 30 min at pH 7.2 and 7.0.

For a more detailed observation of the interaction between the nanoparticles and the cells, Carrier 4 was loaded with adriamycin (ADR) as a fluorescence probe, and the interaction with cells was monitored by flow cytometry analysis. At pH 7.0 Carrier 4 showed more internalization than at pH 7.2, because the biotin was shielded at pH 7.2, but exposed on the surface of micelles at pH 7.0 (FIG. 7).

Fluorescence Microscopy of MCf-7/ADRR Cells

Fluorescence microscopy of MCF-7 cells was used to visualize this interaction. For Carrier 4, the luminescence images clearly distinguished the pH effect. At pH 7.0 and pH 6.8, the cells strongly luminesced, while at pH 7.4 and pH 7.2 the cells showed vague emission. In addition, the images suggested that Carrier 4 at pH 7.0 and pH 6.8 was internalized into the cells (FIGS. 8A-L).

The internalization of drug carriers is one of the important routes to enhancing the cytotoxic effect of the drug. The higher intracellular content of a drug taken up via endocytosis of a carrier may remarkably amplify the cytotoxic effect against the target cells, providing that the carrier structure remained intact with a high drug loading content until intracellular localization. This is unlikely with pH-sensitive liposomes, as is has been reported that such liposomes, without a specific ligand, failed to deliver the contents to the cytoplasm of cells.

To confirm the accompaniment of ADR with Carrier 4 into the cytoplasm at pH 7.0 and 6.8, the internalization of FITC-labeled Carrier 4 loaded with ADR was monitored. FIGS. 8A-L represent the confocal micrographs of the cells after incubation with the nanoparticles. The green color image from FITC-labeled Carrier 4, red image from ADR, and orange color from blended (overlapped) green and red, were observed in the cytoplasm. In the case of Carrier 5, the green color image from FITC-labeled Carrier 4, red image from ADR, and orange color from blended (overlapped) green and red, were found near the cell membranes and in the cytoplasm (FIGS. 9A-L). This result is due to the lack of fusogenic effect of the PLLA-PEG copolymer.

pH-Responsive Cytotoxicity of Carrier 4

Figure 10:
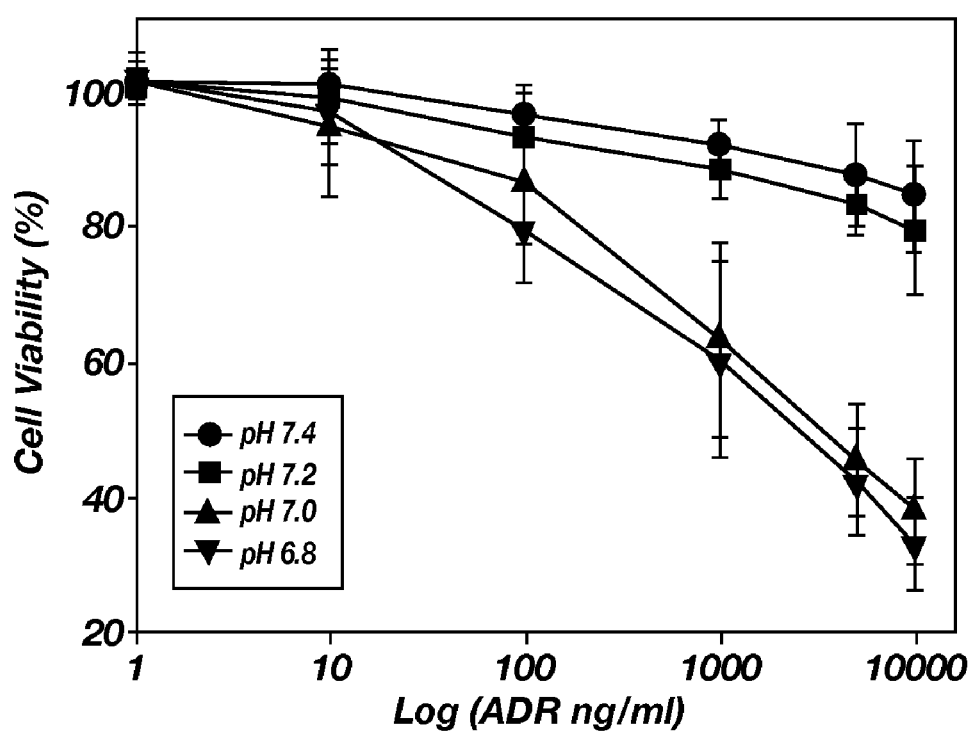
FIG. 10 shows cell viability of ADR-loaded Carrier 4 against MCf-7/ADR$^R$ cells at pH 7.4 (●), pH 7.2 (■), pH 7.0 (▲), and pH 6.8 (▼)

The in vitro cytotoxicity to MCF-7 cells at different pHs (7.4, 7.2, 7.0 and 6.8) were compared in FIG. 10. At pH 7.4 and 7.2, there was no noticeable difference in the cytotoxicity of Carrier 4 at the ADR concentration range of 1 ng/mL to 10,000 ng/mL. However, at pH 7.0 and 6.8, ADR-loaded Carrier 4 showed significantly enhanced cytotoxicity.

In summary, these results support that at pH 7.0 and 6.8, Carrier 4 was associated with the cells and internalized together with the entrapped drug in the cytoplasm, via endocytic mechanism. The improved interaction and internalization of Carrier 4 at tumor pH led to the improvement of cytotoxicity.

The invention claimed is:

1. A drug delivery composition comprising
   (a) a mixed polymeric micelle comprising an inner core and an outer shell, wherein the mixed polymeric micelle comprises a mixture of
      (i) an amphiphilic block copolymer comprising
         an AB-block copolymer comprising a poly(ethylene glycol)-poly(L-histidine) block copolymer or a poly(ethylene glycol)-poly(L-lactic acid) block copolymer or a poly(ethylene glycol)-poly(lactic acid-co-glycolic acid) block copolymer, or
         an ABA-block copolymer comprising a poly(ethylene glycol)-poly(L-lactic acid)-poly(ethylene glycol) block copolymer or a poly(ethylene glycol)-poly(lactic acid-co-glycolic acid)-poly(ethylene glycol) block copolymer, or
         a BAB-block copolymer comprising a poly(L-lactic acid)-poly(ethylene glycol)-poly(L-lactic acid) block copolymer or a poly(lactic acid-co-glycolic acid)-poly(ethylene glycol)-poly(lactic acid-co-glycolic acid) block copolymer, or
         an $(AB)_n$ alternating multiblock copolymer comprising a $(poly(ethylene\ glycol)\text{-}poly(L\text{-}lactic\ acid))_n$ alternating multiblock copolymer or a $(poly(ethylene\ glycol)\text{-}poly(lactic\ acid\text{-}co\text{-}glycolic\ acid))_n$ alternating multiblock copolymer, and
      (ii) a pH-sensitive block copolymer having a ligand covalently bonded thereto, wherein the pH-sensitive block copolymer comprises an extended configuration at less than about pH 7.0 and a globular configuration at about pH 7.4 or greater, and wherein the pH-sensitive block copolymer having a ligand covalently bonded thereto comprises
         a ligand/AB-block copolymer comprising a ligand-poly(L-histidine)-poly(L-lactic acid) block copolymer or a ligand-poly(L-histidine)-poly(lactic acid-co-glycolic acid) block copolymer, or
         a ligand/ABA-block copolymer comprising a ligand-poly(L-histidine)-poly(ethylene glycol)-poly(L-histidine) block copolymer, or
         a ligand/BAC-block copolymer comprising a ligand-poly(ethylene glycol)-poly(L-histidine)-poly(L-lactic acid) block copolymer or a ligand-poly(ethylene glycol)-poly(L-histidine)-poly(lactic acid-co-glycolic acid) block copolymer, or
         a ligand/BABA-block copolymer comprising a ligand-poly(ethylene glycol)-poly(L-histidine)-poly(ethylene glycol)-poly(L-histidine) block copolymer, or
         a ligand/BABC-block copolymer comprising a ligand-poly(ethylene glycol)-poly(L-histidine)-poly(ethylene glycol)-poly(L-lactic acid) or a ligand-poly(ethylene glycol)-poly(L-histidine)-poly(ethylene glycol)-poly(lactic acid-co-glycolic acid), or
         a ligand/block copolymer comprising a ligand-poly(L-histidine)-poly(ethylene glycol)-poly(L-lactic acid) block copolymer; and
   (b) a drug disposed in the inner core.

2. The drug delivery composition of claim 1 wherein the pH-sensitive block copolymer comprises a portion thereof that is hydrophobic at about pH 7.4 or greater and hydrophilic at less than about pH 7.0.

3. The drug delivery composition of claim 1 wherein the pH-sensitive block copolymer comprises the ligand-poly(L-histidine)-poly(L-lactic acid) block copolymer.

4. The drug delivery composition of claim 1 wherein the pH-sensitive block copolymer comprises the ligand-poly(L-histidine)-poly(lactic acid-co-glycolic acid) block copolymer.

5. The drug delivery composition of claim 1 wherein the pH-sensitive block copolymer comprises the ligand-poly(L-histidine)-poly(ethylene glycol)-poly(L-histidine) block copolymer.

6. The drug delivery composition of claim 1 wherein the pH-sensitive block copolymer comprises the ligand-poly(ethylene glycol)-poly(L-histidine)-poly(L-lactic acid) block copolymer.

7. The drug delivery composition of claim 1 wherein the pH-sensitive block copolymer comprises the ligand-poly(ethylene glycol)-poly(L-histidine)-poly(lactic acid-co-glycolic acid) block copolymer.

8. The drug delivery composition of claim 1 wherein the pH-sensitive block copolymer comprises the ligand-poly(ethylene glycol)-poly(L-histidine)-poly(ethylene glycol)-poly(L-histidine) block copolymer.

9. The drug delivery composition of claim 1 wherein the pH-sensitive block copolymer comprises the ligand-poly(L-histidine)-poly(ethylene glycol)-poly(L-lactic acid) block copolymer.

10. The drug delivery composition of claim 1 wherein the pH-sensitive block copolymer comprises the ligand-poly(ethylene glycol)-poly(L-histidine)-poly(ethylene glycol)-poly(L-lactic acid) block copolymer.

11. The drug delivery composition of claim 1 wherein the pH-sensitive block copolymer comprises the ligand-poly(ethylene glycol)-poly(L-histidine)-poly(ethylene glycol)-poly(lactic acid-co-glycolic acid) block copolymer.

12. The drug delivery composition of claim 1 wherein the amphiphilic copolymer comprises the poly(ethylene glycol)-poly(L-lactic acid) block copolymer.

13. The drug delivery composition of claim 1 wherein the amphiphilic copolymer comprises the poly(ethylene glycol)-poly(lactic acid-co-glycolic acid) block copolymer.

14. The drug delivery composition of claim 1 wherein the amphiphilic copolymer comprises the poly(ethylene glycol)-poly(L-histidine) block copolymer.

15. The drug delivery composition of claim 1 wherein the amphiphilic copolymer comprises the poly(ethylene glycol)-poly(L-lactic acid)-poly(ethylene glycol) block copolymer.

16. The drug delivery composition of claim 1 wherein the amphiphilic copolymer comprises the poly(ethylene glycol)-poly(lactic acid-co-glycolic acid)-poly(ethylene glycol) block copolymer.

17. The drug delivery composition of claim 1 wherein the amphiphilic copolymer comprises the poly(L-lactic acid)-poly(ethylene glycol)-poly(L-lactic acid) block copolymer.

18. The drug delivery composition of claim 1 wherein the amphiphilic copolymer comprises the poly(lactic acid-co-glycolic acid)-poly(ethylene glycol)-poly(lactic acid-co-glycolic acid) block copolymer.

19. The drug delivery composition of claim 1 wherein the amphiphilic copolymer comprises the (poly(ethylene glycol)-poly(L-lactic acid))$_n$ alternating multiblock copolymer.

20. The drug delivery composition of claim 1 wherein the amphiphilic copolymer comprises the (poly(ethylene glycol)-poly(lactic acid-co-glycolic acid))$_n$ alternating multiblock copolymer.

21. The drug delivery composition of claim 1 wherein the amphiphilic block copolymer comprises the poly(ethylene glycol)-poly(L-lactic acid) block copolymer, and the pH-sensitive block copolymer comprises the ligand-poly(L-histidine)-poly(ethylene glycol)-poly(L-lactic acid) block copolymer.

22. The drug delivery composition of claim 1 wherein the amphiphilic block copolymer comprises the poly(ethylene glycol)-poly(L-histidine) block copolymer, and the pH-sensitive block copolymer comprises the ligand-poly(L-histidine)-poly(ethylene glycol)-poly(L-lactic acid) block copolymer.

23. The drug delivery composition of claim 1 wherein the ligand comprises folate.

24. The drug delivery composition of claim 1 wherein the ligand comprises biotin.

* * * * *